US00PP22010P2

(12) United States Plant Patent
Herrera Valenzuela et al.

(10) Patent No.: US PP22,010 P2
(45) Date of Patent: Jul. 5, 2011

(54) ***ALSTROEMERIA* PLANT NAMED 'JAMOA'**

(50) Latin Name: *Alstroemeria hybrida*
Varietal Denomination: Jamoa

(75) Inventors: Camilo Herrera Valenzuela, Bogotá (CO); Henry Belalcázar Valencia, Bogotá (CO)

(73) Assignee: C.I. Valmar S.A., Bogotá (CO)

( * ) Notice: Subject to any disclaimer, the term of this patent is extended or adjusted under 35 U.S.C. 154(b) by 0 days.

(21) Appl. No.: 12/660,105

(22) Filed: Feb. 19, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner* — June Hwu
(74) *Attorney, Agent, or Firm* — C. A. Whealy

(57) ABSTRACT

A new and distinct cultivar of *Alstroemeria* plant named 'Jamoa', characterized by its erect and strong flowering stems; vigorous growth habit; large purple and white-colored flowers with purple-colored flecks and streaks, flowers arranged in symmetrical umbels; and excellent postproduction longevity.

1 Drawing Sheet

Botanical designation: *Alstormeria hybrida.*
Cultivar denomination: 'JAMOA'.

BACKGROUND OF THE INVENTION

The present invention relates to a new and distinct cultivar of *Alstroemeria* plant, botanically known as *Alstroemeria hybrida*, commercially used as a cut flower *Alstroemeria*, and hereinafter referred to by the name 'Jamoa'.

The new *Alstroemeria* plant is a product of a planned breeding program conducted by the Inventors in Madrid, Cundinamarca, Colombia. The objective of the breeding program was to create new *Alstroemeria* cultivars with desirable plant qualities, attractive flower color and excellent postproduction longevity.

The new *Alstroemeria* plant originated from a cross-pollination conducted by the Inventors in Madrid, Cundinamarca, Colombia in February, 2004 of a proprietary selection of *Alstroemeria hybrida* identified as code number PJA 858, not patented, as the female, or seed, parent with a proprietary selection of *Alstroemeria hybrida* identified as code number HH 325, as the male, or seed, parent. The new *Alstroemeria* plant was discovered and selected by the Inventors as a single flowering plant from within the progeny of the stated cross-pollination grown in a controlled greenhouse environment in Madrid, Cundinamarca, Colombia in April, 2005.

Asexual reproduction of the new *Alstroemeria* plant by rhizome divisions in a controlled greenhouse environment in Madrid, Cundinamarca, Colombia since June, 2005, has shown that the unique features of this new *Alstroemeria* plant are stable and reproduced true to type in successive generations.

SUMMARY OF THE INVENTION

Plants of the new *Alstroemeria* have not been observed under all possible environmental and cultural conditions. The phenotype may vary somewhat with variations in environment and cultural practices such as temperature and light intensity without, however, any variance in genotype.

The following traits have been repeatedly observed and are determined to be the unique characteristics of 'Jamoa'. These characteristics in combination distinguish 'Jamoa' as a new and distinct cultivar of *Alstroemeria* plant:

1. Erect and strong flowering stems.
2. Vigorous growth habit.
3. Large purple and white-colored flowers with purple-colored flecks and streaks, flowers arranged in symmetrical umbels.
4. Excellent postproduction longevity.

Plants of the new *Alstroemeria* can be compared to plants of the parent selections. Plants of the new *Alstroemeria* differ from plants of the parent selections primarily in flower color as plants of the female parent selection have pink-colored flowers and plants of the male parent selection have red purple-colored flowers. In addition, perianth segments of plants of the new *Alstroemeria* are more deeply emarginate than perianth segments of plants of the male parent selection.

Plants of the new *Alstroemeria* can be compared to plants of *Alstroemeria hybrida* 'Tescupi', not patented. In side-by-side comparisons plants of the new *Alstroemeria* differed primarily from plants of 'Tescupi' in the following characteristics:

1. Plants of the new *Alstroemeria* had slightly smaller umbels than plants of 'Tescupi'.
2. Plants of the new *Alstroemeria* had more flowers per inflorescence than plants of 'Tescupi'.
3. Plants of the new *Alstroemeria* had smaller and more rounded flowers than plants of 'Tescupi'.
4. Plants of the new *Alstroemeria* and 'Tescupi' differed in flower color.
5. Perianth segments of plants of the new *Alstroemeria* were more deeply emarginate than perianth segments of plants of 'Tescupi'.
6. Plants of the new *Alstroemeria* and 'Tescupi' differed in anther and pollen color.
7. Plants of the new *Alstroemeria* and 'Tescupi' differed in ovary color.
8. Plants of the new *Alstroemeria* had shorter pedicels than plants of 'Tescupi'.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria* plant.

The photograph at the bottom of the sheet comprises a side perspective view of a typical flowering stem of 'Jamoa'.

The photograph at the top of the sheet is a close-up view of a typical inflorescence of 'Jamoa'.

DETAILED BOTANICAL DESCRIPTION

The aforementioned photographs and following observations and measurements describe plants of the new *Alstroemeria* grown in Madrid, Cundinamarca, Colombia in a polyethylene-covered greenhouse in ground beds. During the production of the plants, maximum day temperatures averaged 31.5° C., maximum night temperatures averaged 6° C. and light levels averaged 21.4 KWH/m$^2$. Plants used for the photographs and description were two years old. Color references are made to The Royal Horticultural Society Colour Chart, 2007 Edition, except where general terms of ordinary dictionary significance are used.

Botanical classification: *Alstroemeria hybrida* 'Jamoa'.

Parentage:

*Female, or seed, parent.*—Proprietary selection of *Alstroemeria hybrida* identified as code number PJA 858, not patented.

*Male, or pollen, parent.*—Proprietary selection of *Alstroemeria hybrida* identified as code number HH 325.

Propagation:

*Type.*—By rhizome divisions.

*Time to initiate roots.*—About two weeks at temperatures ranging from about 6° C. to 32° C.

*Time to produce a rooted young plant.*—About eight weeks at temperatures ranging from about 6° C. to 32° C.

*Root description.*—Fleshy, medium in thickness; close to 155A in color.

*Rooting habit.*—Freely branching; dense.

*Rhizomes.*—Shape: Rounded. Length: About 6 cm. Diameter: About 1.28 cm. Texture: Fleshy. Color: Close to NN155C.

Plant description:

*Plant and growth habit.*—Upright; freely branching, bushy appearance; vigorous growth habit.

*Time from planting to harvest of cut flowers.*—About 20 weeks.

Flowering stem description:

*Aspect.*—Erect.

*Length.*—About 110 cm to 115 cm.

*Diameter.*—About 6 mm.

*Internode length.*—About 3.2 cm to 6.5 cm.

*Strength.*—Strong.

*Texture.*—Smooth, glabrous.

*Color.*—Close to 144A.

Foliage description:

*Arrangement.*—Alternate, simple.

*Length.*—About 11.5 cm.

*Width.*—About 3.8 cm.

*Shape.*—Oblanceolate.

*Apex.*—Acute.

*Base.*—Attenuate.

*Margin.*—Entire.

*Texture, upper and lower surfaces.*—Smooth, glabrous; longitudinally ridged.

*Venation pattern.*—Parallel.

*Color.*—Developing leaves, upper surface: Close to 137C. Developing leaves, lower surface: Close to 137B. Fully expanded leaves, upper surface: Close to N137B; venation, close to 137B. Fully expanded leaves, lower surface: Close to 137B; venation, close to 137C.

*Petioles.*—Length: About 2.5 cm. Diameter: About 8 mm. Texture, upper and lower surfaces: Smooth, glabrous. Color, upper and lower surfaces: Close to 137B.

Flower description:

*Flower type and arrangement.*—Single cup-shaped flowers arranged in compound umbels; flowers face upright to outwardly; perianth segments separate.

*Flowering habit.*—Freely flowering with about 15 open flowers and flower buds per inflorescence.

*Natural flowering season.*—Flowering continuous year round in a greenhouse in Colombia; plants begin flowering about 20 weeks after planting.

*Fragrance.*—None detected.

*Flower longevity as a cut flower.*—About two weeks; flowers not persistent.

*Flower buds* (*showing color*).—Length: About 3.2 cm. Diameter: About 1.4 cm. Shape: Obovate. Color: Close to 144B to 144D; towards the apex, close to 144A.

*Umbel height.*—About 13 cm.

*Umbel diameter.*—About 14 cm by 16 cm.

*Flower diameter.*—About 5.5 cm.

*Flower length* (*height*).—About 5 cm.

*Flower depth.*—About 5.6 cm.

*Perianth.*—Arrangement: Six arranged in two whorls, each whorl with two lateral and one median segments. Inner perianth, lateral segments: Length: About 5.4 cm. Width: About 1.6 cm. Shape: Oblanceolate. Apex: Apiculate. Base: Attenuate. Margin: Entire; towards the apex, slightly sinuate. Texture, upper and lower surfaces: Smooth, glabrous; satiny. Color, when opening, upper surface: Close to NN155B; at the apex, close to 186C; flecks and streaks, close to 187C. Color, when opening, lower surface: Close to NN155B; at the apex, close to 186D; venation, close to 145C. Color, fully opened, upper surface: Close to 71A to 71B; towards the center, close to 71D; mid-section and base, close to 155A to 155B; flecks, close to 183A; with development, apices become closer to 70B to 70C. Color, fully opened, lower surface: Close to 71C to 71D; mid-section, close to 155B to 155C; towards the base, close to 155B to 155C tinted with close to 72D; with development, apices become closer to 70B to 70C. Inner perianth, median segment: Length: About 4.4 cm. Width: About 1.6 cm. Shape: Oblanceolate. Apex: Apiculate. Base: Attenuate. Margin: Entire; towards the apex, slightly sinuate. Texture, upper and lower surfaces: Smooth, glabrous; satiny. Color, when opening, upper surface: Close to 145C to 145D; margins tinted with close to 186D; at the base, close to 145B. Color, when opening, lower surface: Close to 145D; at the base, close to 145A; venation, close to 145B. Color, fully opened, upper surface: Close to 71A to 71B; towards the center, close to 71D; mid-section and base, close to NN155C;

at the base, close to 145A; with development, apices become closer to 70B to 70C. Color, fully opened, lower surface: Close to 71C to 71D; mid-section, close to NN155C; towards the base, close to 144B; with development, apices become closer to 70B to 70C. Outer perianth, lateral segments: Length: About 5.2 cm. Width: About 2.4 cm. Shape: Obovate. Apex: Emarginate to mucronate. Base: Attenuate. Margin: Entire; towards the apex, slightly sinnuate. Texture, upper and lower surfaces: Smooth, glabrous. Color, when opening, upper surface: Close to NN155B; center and towards the apex, close to 144B; towards the margins, close to 70B. Color, when opening, lower surface: Close to NN155C; center, close to 144A; towards the margins, close to 70B to 70C. Color, fully opened, upper surface: Close to NN155C; towards the margins, close to 71A to 71C; apex and margins becoming closer to 68B with development. Color, fully opened, lower surface: Close to 71C to 71D; at the apex and center, close to 146D; apex and margins becoming closer to 68D with development. Outer perianth, median segment: Length: About 4.8 cm. Width: About 2.4 cm. Shape: Obovate. Apex: Emarginate to mucronate. Base: Attenuate. Margin: Entire; towards the apex, slightly sinnuate. Texture, upper and lower surfaces: Smooth, glabrous. Color, when opening, upper surface: Close to NN155B; center and towards the apex, close to 144B; towards the margins, close to 70B. Color, when opening, lower surface: Close to NN155C; center, close to 144A; towards the margins, close to 70B to 70C. Color, fully opened, upper surface: Close to NN155C; towards the margins, close to 71A to 71C; apex and margins becoming closer to 68B with development. Color, fully opened, lower surface: Close to 71C to 71D; at the apex and center, close to 146D; apex and margins becoming closer to 68D with development.

*Pedicels.*—Length: About 3.3 cm. Diameter: About 2.5 mm. Strength: Strong. Angle: About 15° to 25° from the peduncle axis. Texture: Smooth, glabrous. Color: Close to 146C.

*Reproductive organs.*—Stamens: Quantity per flower: Six. Anther shape: Elongated. Anther length: About 8 mm. Anther diameter: About 3 mm. Anther color: Close to 199B. Pollen amount: Moderate. Pollen color: Close to 197B. Pistils: Quantity per flower: One. Pistil length: About 4.6 cm. Style length: About 3.4 cm. Style color: Close to 186D; towards the base, close to NN155C. Stigma shape: Three-parted. Stigma color: Close to 185D. Ovary color: Close to 144A.

*Fruit/seed.*—Fruit and seed development has not been observed.

Disease/pest resistance: Plants of the new *Alstroemeria* have not been observed to be resistant to pathogens and pests common to *Alstroemeria*.

It is claimed:

1. A new and distinct *Alstroemeria* plant named 'Jamoa' as illustrated and described.

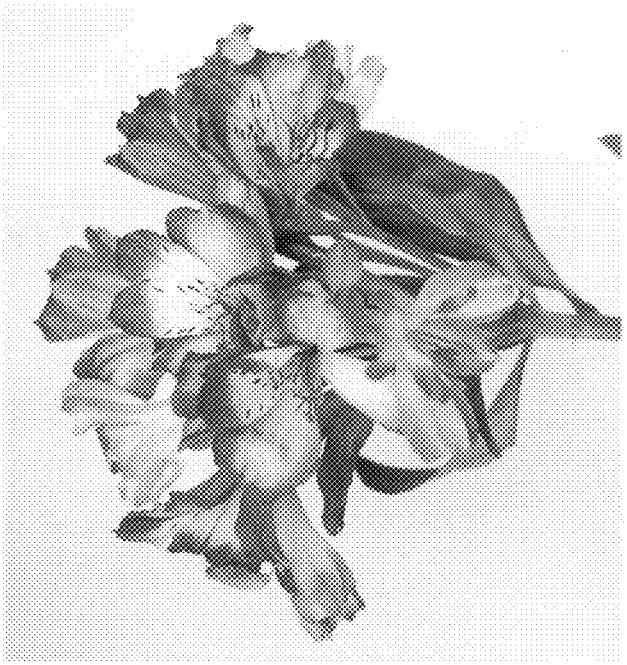
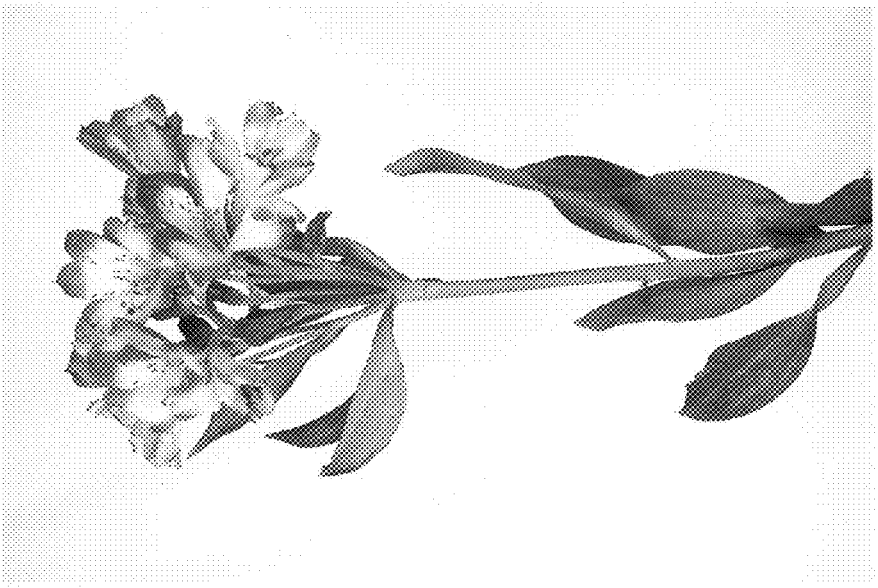

* * * * *